United States Patent
Patron et al.

(10) Patent No.: US 6,530,373 B1
(45) Date of Patent: Mar. 11, 2003

(54) RESPIRATOR MASK

(75) Inventors: Anthony P. Patron, San Francisco, CA (US); Michael Sullivan, Deephaven, MN (US); Gary L. Hansen, Eden Prairie, MN (US); Bradley J. Bonnette, Minneapolis, MN (US); John W. Lai, San Francisco, CA (US); Christine G. Kronich, St. Paul, MN (US); Steven S. Bordewick, Shoreview, MN (US); Clifford T. Jue, Santa Cruz, CA (US); Dan P. Wilkins, Arroyo Grande, CA (US); Jeff C. Weintraub, Boulder Creek, CA (US)

(73) Assignee: Mallinckrodt Inc., St. Louis, MO (US)

( * ) Notice: Subject to any disclaimer, the term of this patent is extended or adjusted under 35 U.S.C. 154(b) by 114 days.

(21) Appl. No.: 09/632,625

(22) Filed: Aug. 4, 2000

(51) Int. Cl.$^7$ ............................................. A62B 18/02
(52) U.S. Cl. ........................... 128/205.25; 128/206.24; 128/206.21
(58) Field of Search ................. 128/200.24, 200.27, 128/201.12, 201.15, 201.19, 201.22, 201.25, 203.29, 205.25, 206.12–206.28, 207.11, 207.17, 207.18

(56) References Cited

U.S. PATENT DOCUMENTS

| | | |
|---|---|---|
| 3,330,273 A | 7/1967 | Bennett |
| 3,545,436 A | 12/1970 | Holloway |
| 4,167,185 A | 9/1979 | Lewis |
| 4,296,746 A | 10/1981 | Mason, Jr. et al. |
| 4,677,977 A | 7/1987 | Wilcox |
| 4,739,755 A | 4/1988 | White et al. |
| 4,782,832 A | 11/1988 | Trimble et al. |
| 4,907,584 A | 3/1990 | McGinnis |
| 4,971,051 A | 11/1990 | Toffolon |
| 5,074,297 A | 12/1991 | Venegas |
| 5,243,971 A | 9/1993 | Sullivan et al. |
| 5,441,046 A | 8/1995 | Starr et al. |

(List continued on next page.)

FOREIGN PATENT DOCUMENTS

| | | |
|---|---|---|
| DE | 37 07 952 | 9/1998 |
| EP | 0 072 220 | 2/1983 |
| EP | 0 462 701 | 12/1991 |
| WO | WO 98/04310 | 2/1998 |
| WO | WO 98/34665 | 8/1998 |

OTHER PUBLICATIONS

Burgess et al., "Performance and Acceptance of Respirator Facial Seals" *Ergonomics* 13(4):455–464 (1970).

*Primary Examiner*—Glenn K. Dawson
(74) *Attorney, Agent, or Firm*—Rothwell, Figg, Ernst & Manbeck

(57) ABSTRACT

A respirator mask seal and shell are provided according to one embodiment of the invention. The respirator mask seal and shell includes a mask shell having a face opening, a slot for air passage, and at least one attachment portion spaced around the face opening. They also include a movable interface having a hose connector and a contoured opening adapted to fit against the mask shell. The contoured opening is slidable over the slot and is capable of being positioned on the mask shell. The mask seal has a flexible sidewall having distal and proximal ends and includes a rounded outer seal portion located on the distal end of the sidewall, a rounded inner seal portion located between the distal and proximal ends, and a support ring embedded in the sidewall. The inner seal portion is thicker than the outer seal portion and is non-continuous. The support ring includes at least one attachment portion adapted to engage the at least one attachment portion of the mask shell. The mask seal is capable of being removably affixed to the mask shell. The movable interface is capable of being positionally adjusted on the mask shell and the mask seal is capable of being inwardly deformed by contact with a face region of the user.

24 Claims, 16 Drawing Sheets

U.S. PATENT DOCUMENTS

| | | |
|---|---|---|
| 5,492,116 A | 2/1996 | Scarberry et al. |
| 5,503,147 A | 4/1996 | Bertheau |
| 5,517,986 A | 5/1996 | Starr et al. |
| 5,537,994 A | 7/1996 | Thornton |
| 5,538,000 A | 7/1996 | Rudolph |
| 5,540,223 A | 7/1996 | Starr et al. |
| RE35,339 E | 10/1996 | Rapoport |
| 5,560,354 A | 10/1996 | Berthon-Jones et al. |
| 5,570,689 A * | 11/1996 | Starr et al. ............. 128/207.11 |
| D377,089 S | 12/1996 | Starr et al. |
| 5,647,357 A * | 7/1997 | Barnett et al. ......... 128/206.24 |
| 5,655,527 A | 8/1997 | Scarberry et al. |
| 5,657,752 A | 8/1997 | Landis et al. |
| 5,662,101 A | 9/1997 | Ogden et al. |
| D385,960 S | 11/1997 | Rudolph |
| 5,724,965 A | 3/1998 | Handke et al. |
| D402,755 S | 12/1998 | Kwok |
| 6,196,223 B1 * | 3/2001 | Belfer et al. ........... 128/206.25 |
| 2001/0032648 A1 * | 10/2001 | Hart ..................... 128/204.23 |

* cited by examiner

RESPIRATOR MASK

BACKGROUND OF THE INVENTION

1. Field of the Invention

The present invention relates generally to the field of respirator masks.

2. Description of the Background Art

A respirator mask is a device used to deliver a gas or gases to a patient. In its simplest form, the respirator mask includes a face piece, an attaching means, and a gas supply hose. The respirator mask may be used to deliver any variety of gases, including air or oxygen, and a variety of medicines or treatments.

The face piece is fitted over a nose and/or mouth portion of the face of the patient. Preferably, the fit of the face piece against the skin of the patient is substantially airtight and does not allow the supplied gas to escape. A strap or other attaching device holds the face piece against the face of the patient in order to deliver the gas to the patient and also ensures that the face piece forms a seal with the face of the patient.

In a related art respirator mask, the face piece is generally formed of a rigid or semi-rigid shell having a facial seal on the edges thereof. The facial seal contacts the face of the wearer, and is made to be somewhat rigid by having thicker walls in places. Sealing is accomplished in the related art respirator mask by the facial seal in conjunction with a shell contour. The shell contour is generally formed in one or more standard sizes and shapes designed to fit the largest number of wearers.

A drawback is that, except for expensive custom made respirator masks, a related art respirator mask does not conform perfectly to an individual user. The sealing material of the related art respirator mask generally can be compressed only a limited amount, and the related art respirator mask does not adapt well to a face different from the shell contour. Therefore, the related art respirator mask may suffer from a poor gas seal and from pressure points against the face.

Another drawback of the related art is the form of attachment of the mask seal to the mask shell. FIG. 1 shows a related art respirator mask shell and mask seal attachment. The respirator mask of the related art includes a mask shell 3 and a mask seal 1. The mask seal 1 of the related art is generally soft and flexible in order to conform to the face of a wearer and must be capable of being attached to the mask shell 3 so that the respirator mask may be disassembled for cleaning, etc. In FIG. 1 a common related art respirator mask includes an arrowhead-shaped portion 4 on the mask shell 3 that fits into a groove or slot in the mask seal 1. See, e.g., U.S. Pat. No. 5,243,971.

The drawback with this seal attachment arrangement is that the seal is difficult to properly align and attach. The user, especially an elderly person, may not have the manual dexterity needed to align and attach the seal to the mask. In addition, the user may not have enough hand strength to push in and complete a seal that is continuous around a perimeter of the mask. If the alignment is not perfect, the seal may be deformed, affecting both the fit and the airtightness of a seal-mask interface and a seal-face interface.

FIGS. 2A–2B show a second related art respirator mask shell and mask seal attachment. The mask shell 3 includes at least one rigid loop 6 and at least one associated barbed tab 7 that fits underneath the rigid loop 6 and is retained by the rigid loop 6. See, e.g., U.S. Pat. No. 5,724,965.

FIGS. 3A–3B show a third related art respirator mask shell and mask seal attachment. The rigid shell 3 includes apertures 10 and the mask seal 1 includes barbed protrusions 11 that extend through and engage in the apertures 10. See, e.g., U.S. Pat. No. 3,330,273.

There remains a need in the art for an improved respirator mask.

SUMMARY OF THE INVENTION

A respirator mask seal and shell are provided according to one embodiment of the invention. The respirator mask seal and shell comprises a mask shell having a face opening, a slot for air passage, and at least one attachment portion spaced around the face opening. The respirator mask seal and shell also comprises a movable interface having a hose connector and a contoured opening adapted to fit against the mask shell. The contoured opening of the movable interface is slidable over the slot and is capable of being positioned on the mask shell over a predetermined range. The respirator mask seal and shell further comprises a mask seal comprising a flexible sidewall having distal and proximal ends and including a rounded outer seal portion located on the distal end of the sidewall, a rounded inner seal portion located between the distal and proximal ends, and a support ring embedded in the sidewall adjacent the proximal end. The inner seal portion is thicker than the outer seal portion and is non-continuous around an inner surface of the mask seal. The support ring includes at least one attachment portion adapted to engage the at least one attachment portion of the mask shell. The proximal end of the mask seal is capable of being removably affixed to the mask shell. The movable interface is capable of being positionally adjusted on the mask shell to suit a wearer. In use, the mask seal is capable of being inwardly deformed by contact with a face region of the user.

A mask seal assembly for a respirator mask is provided according to another embodiment of the invention. The mask seal assembly comprises a mask shell, a mask seal, and a plurality of attachment devices on the mask shell at discrete attachment sites, with the plurality of attachment devices allowing the mask seal to be removably attached to the mask shell.

A seal assembly for a respirator mask is provided according to yet another embodiment of the invention. The seal assembly comprises a mask shell, a support ring, and a mask seal over-molded upon the support ring. The support ring is conformed to assist the mask'seal in retaining a predetermined shape and to facilitate attachment of the mask seal to the mask shell.

A method of creating a seal assembly for a respirator mask is provided according to another embodiment of the invention. The method comprises over-molding an elastomeric mask seal about a support structure to produce a mask seal having an embedded support structure.

A respirator mask is provided according to a further embodiment of the invention. The respirator mask comprises a mask shell having a convex outer surface and a slot therein and a movable interface that movably pivots on the convex outer surface. The movable interface includes a hose connector adapted to receive a gas supply hose and further includes an interior passage that communicates a gas from the hose connector to the slot and to an interior region of the mask shell. The movable interface allows an angular adjustment of the mask shell with respect to a facial plane angle of a user.

The above and other features and advantages of the present invention will be further understood from the fol-

DETAILED DESCRIPTION OF THE PREFERRED EMBODIMENTS

Figure 1:
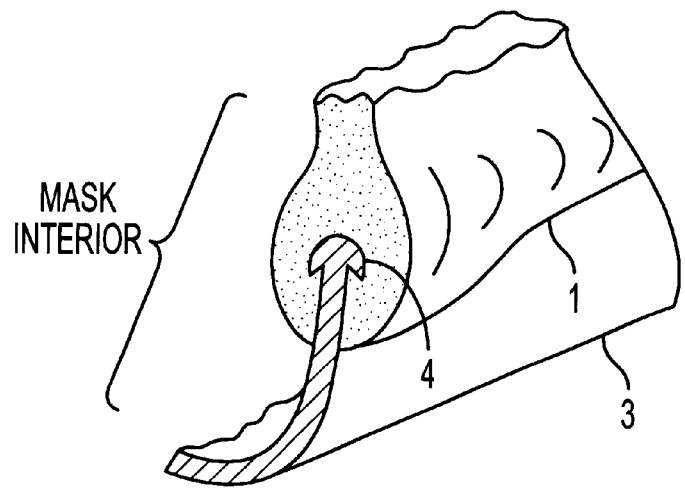
FIG. 1 shows a related art respirator mask shell and mask seal attachment.
Figure 2A:
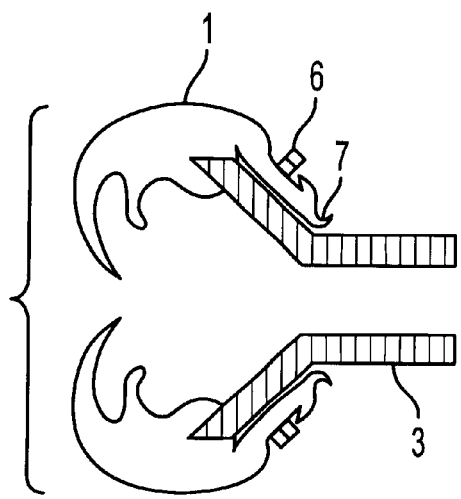
FIGS. 2A–2B show a second related art respirator mask shell and mask seal attachment.
Figure 2B:
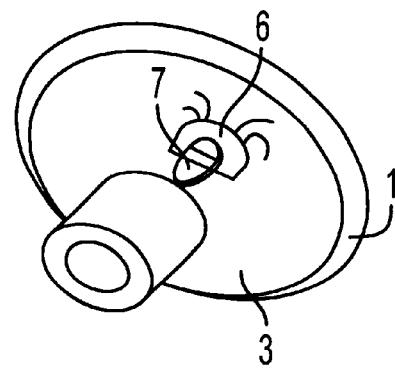
Figure 3A:
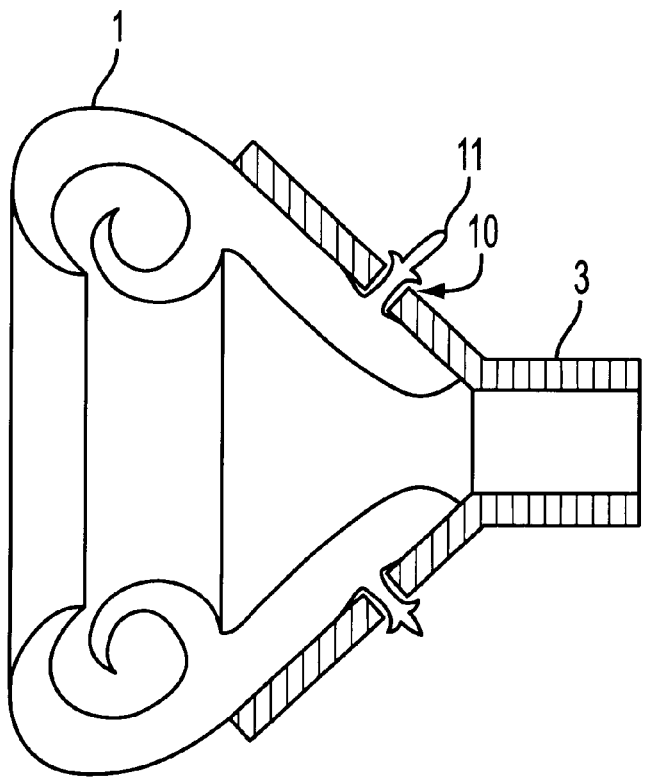
FIGS. 3A–3B show a third related art respirator mask shell and mask seal attachment.
Figure 3B:
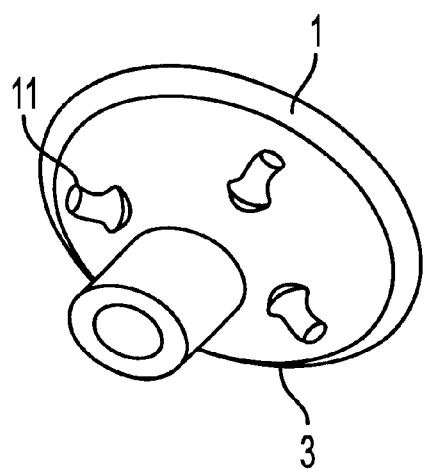
Figure 4A:
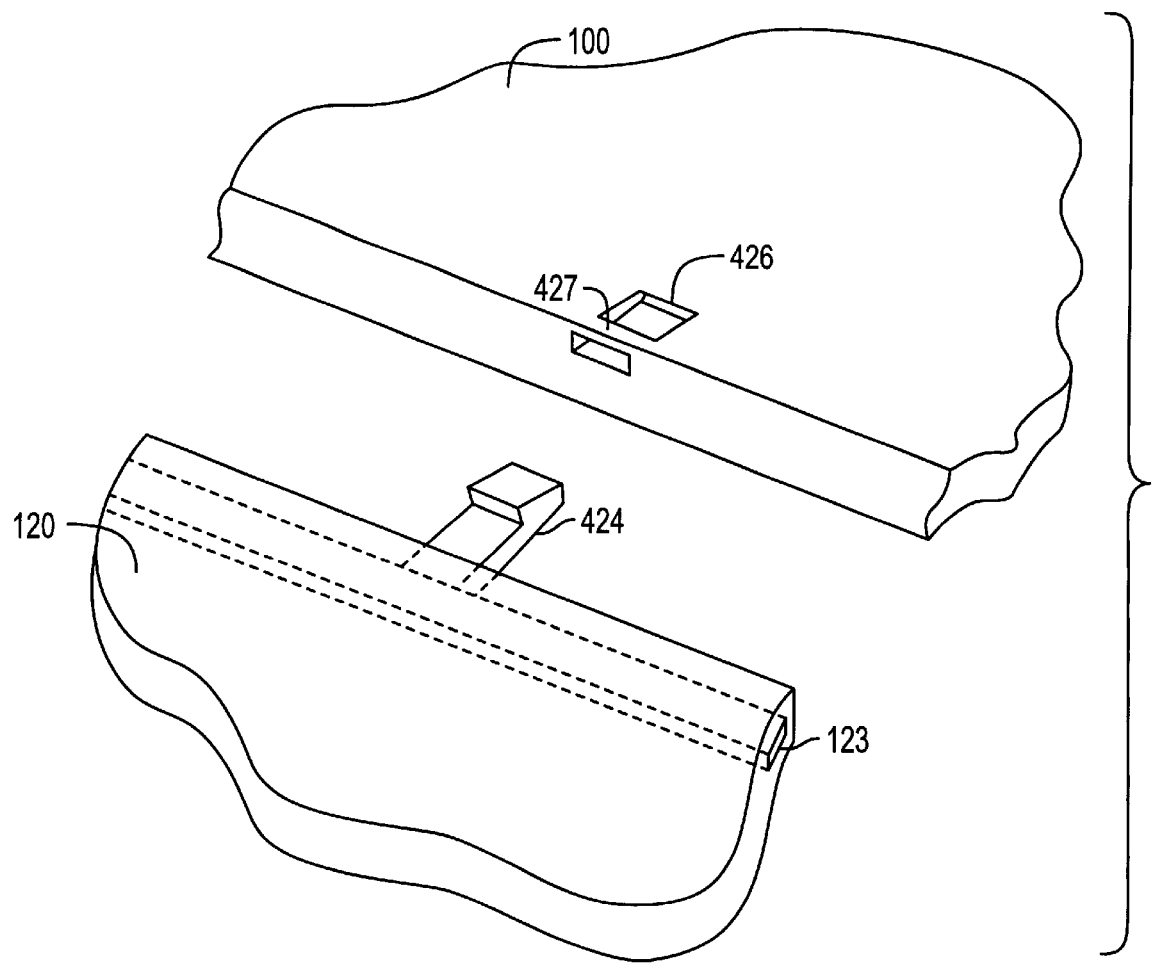
FIGS. 4A–4B show an attachment device of one embodiment of the present invention.
Figure 4B:
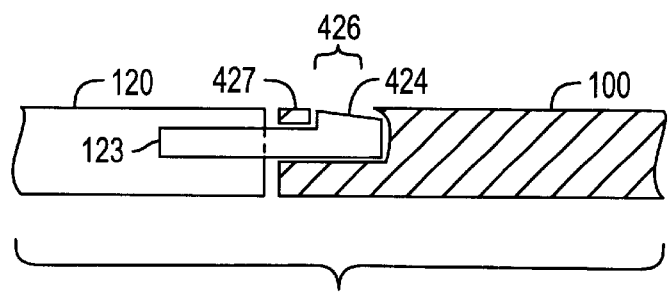

FIGS. 4A–4B show an attachment device of one embodiment of the present invention. In this embodiment a mask seal 120 is attached to a rigid shell 100 (see FIG. 10 for a complete mask illustration). The attachment device includes attachment portions on the mask seal 120 and on the mask shell 100. These attachment portions form discrete attachment sites. Preferably, three such discrete attachment sites are formed on the respirator mask 99 in order to hold the mask seal 120 in a predetermined position on the mask shell 100. However, any number of discrete attachment sites may be used.

In the attachment device shown, the mask seal 120 includes a rigid or semi-rigid support ring 123 (see FIG. 12) that includes an attachment portion in the form of a barb 424. The barb 424 fits within a corresponding attachment portion in the form of an opening 426 that includes a retaining bar 427. The attachment portions may have a width of about 1 millimeter to about 2 centimeters.

Figure 5A:
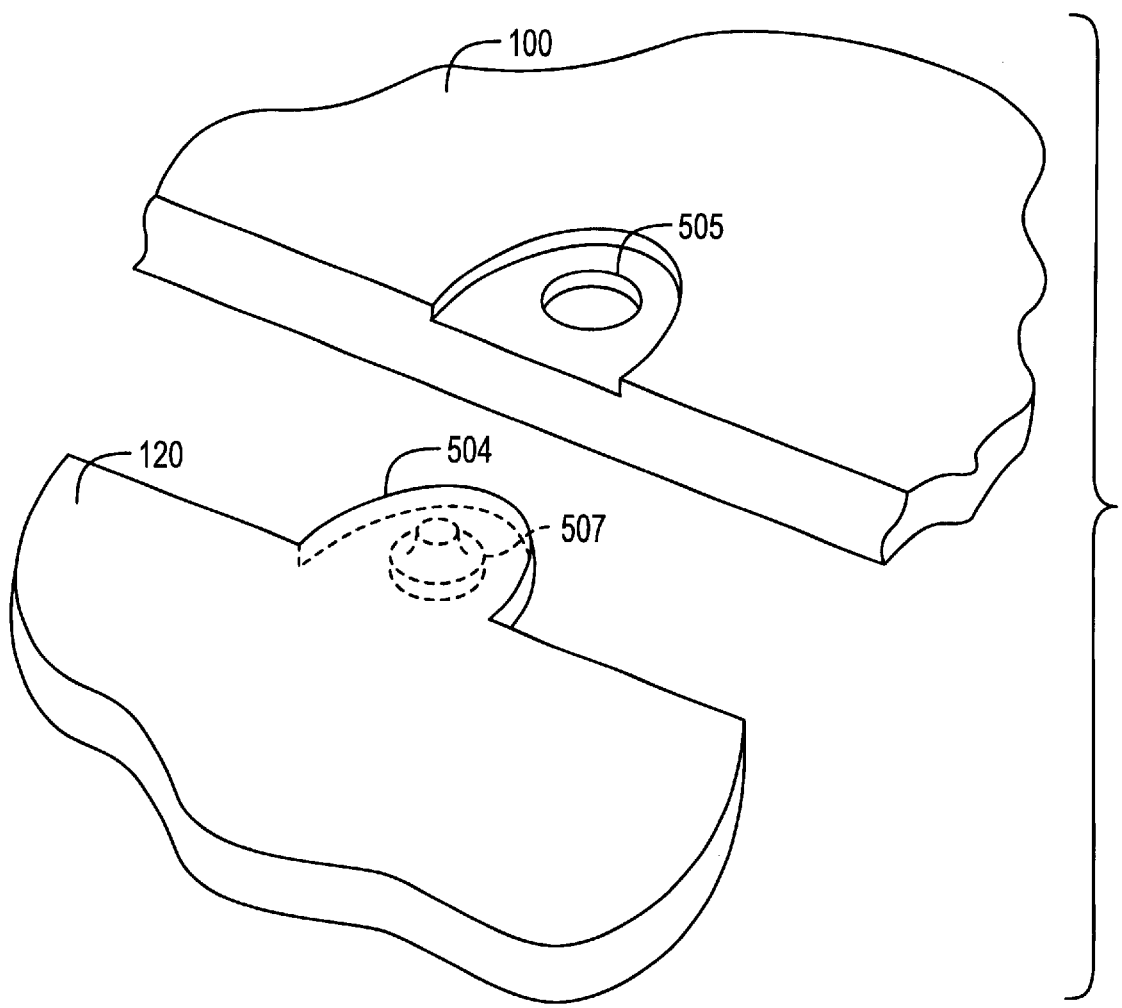
FIGS. 5A–5B show another embodiment of an attachment device of the present invention.
Figure 5B:
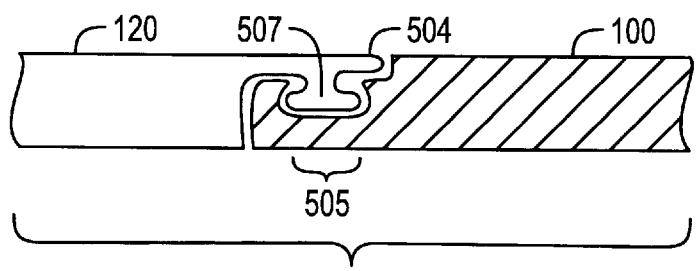

FIGS. 5A–5B show another embodiment of an attachment device of the present invention. In this embodiment, the mask seal 120 includes an attachment portion in the form of an extended portion 504 of the mask seal 120 and a knob 507. The extended portion 504 extends beyond an intersection of the mask seal 120 and the mask shell 100. The knob 507 fits within a corresponding attachment portion in the form of a blind cavity 505 in the mask shell 100. The blind cavity 505 may be substantially hemispherical, with an opening that is smaller than a cavity chamber. The blind cavity 505 does not extend through the mask shell 100. The blind cavity 505 may be recessed into the mask shell 100. The knob 507 is wider than the cavity opening.

Figure 6A:
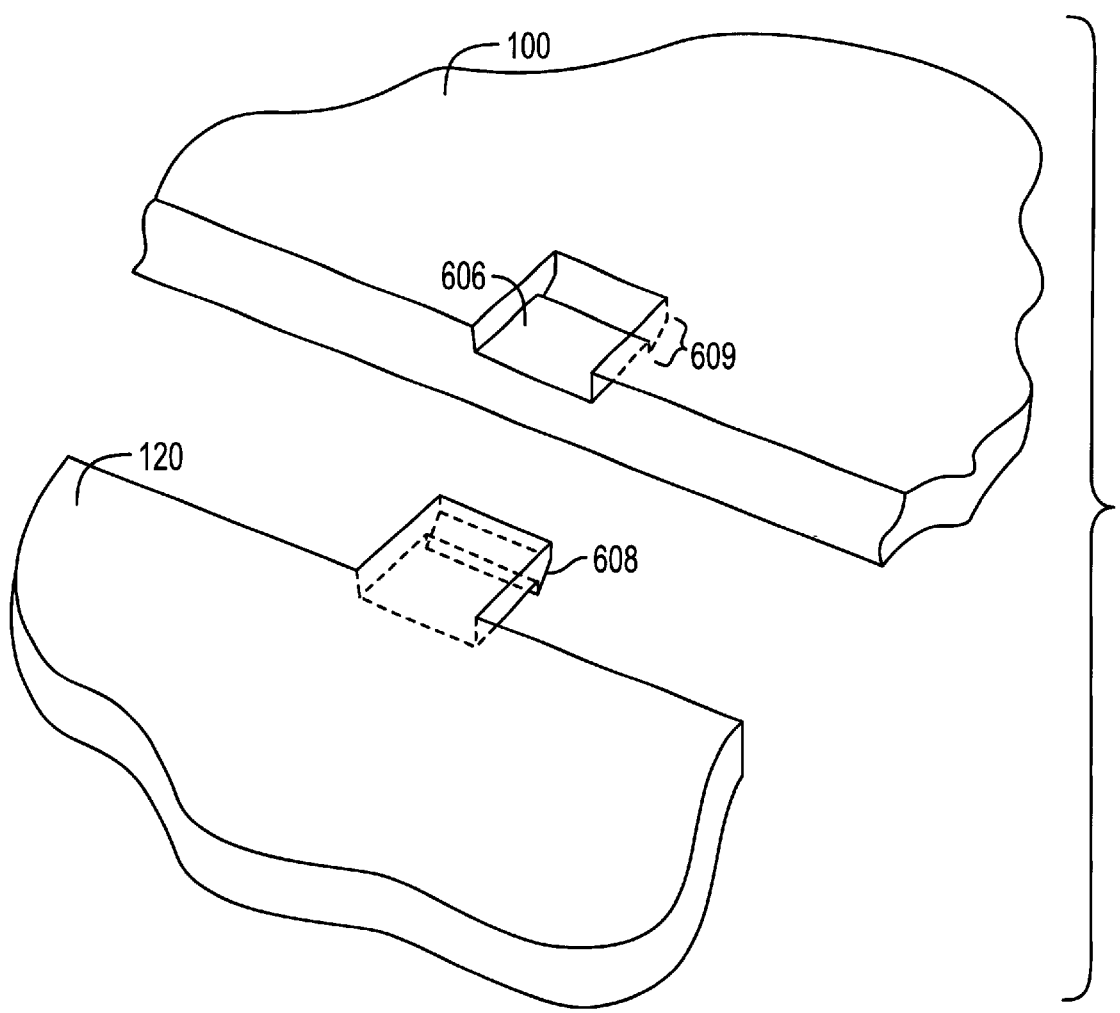
FIGS. 6A–6B show yet another embodiment of an attachment device.
Figure 6B:
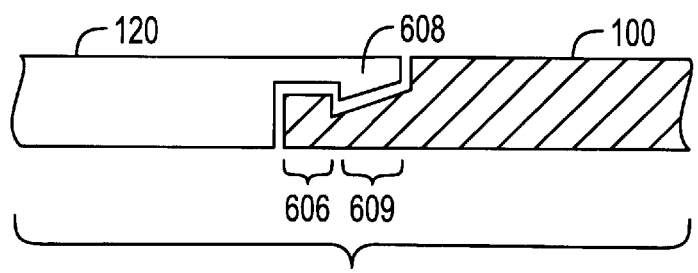

FIGS. 6A–6B show yet another embodiment of an attachment device. This embodiment includes an attachment portion in the form of a barb 608 formed on the mask seal 120. The barb 608 engages a corresponding attachment portion in the form of a cavity 609 and a lip 606 formed in the mask shell 100.

Figure 7A:
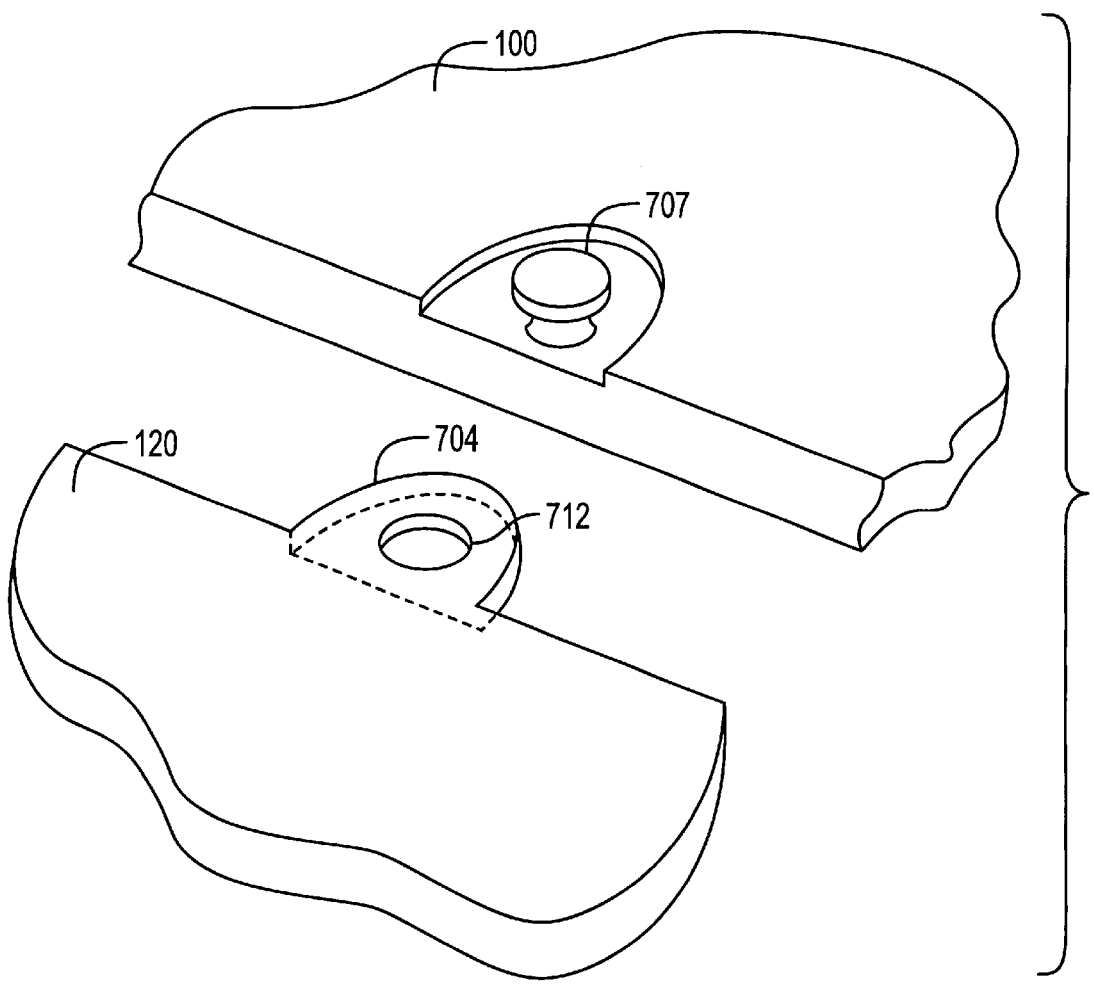
FIGS. 7A–7B show yet another embodiment of an attachment device.
Figure 7B:
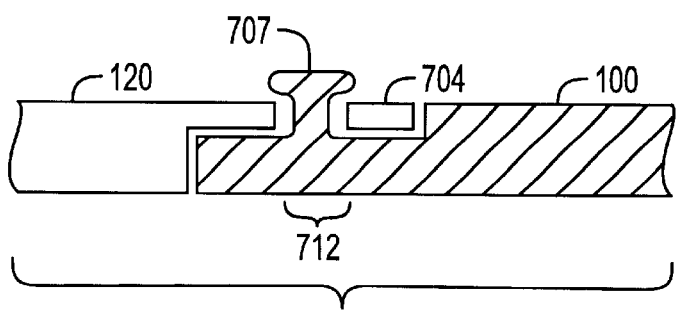

FIGS. 7A–7B show yet another embodiment of an attachment device. In this embodiment the mask seal 120 includes an attachment portion in the form of an extended portion 704 of the mask seal 120 and a hole 712 that extends through the extended portion 704. The extended portion 704 extends beyond an intersection of the mask seal 120 and the mask shell 100. The mask shell 100 includes a corresponding attachment portion in the form of an integral knob 707 that may be pressed through the hole 712. The knob 707 engages the hole 712 to hold the mask seal 120 on the mask shell 100. The knob 707 is wider than the hole 712. The knob 707 may be recessed into the mask shell 100.

Figure 8A:
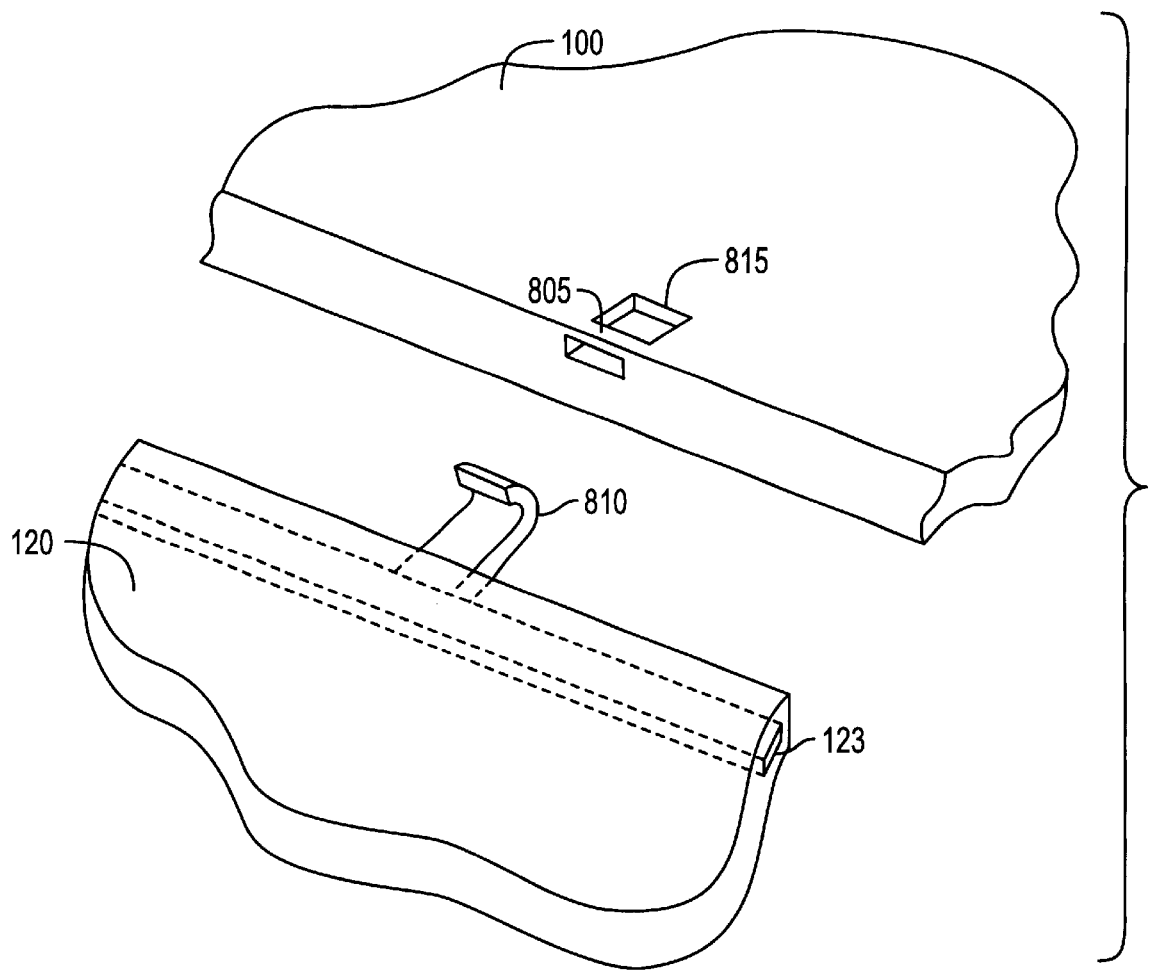
FIGS. 8A–8B show still another embodiment of an attachment device.
Figure 8B:
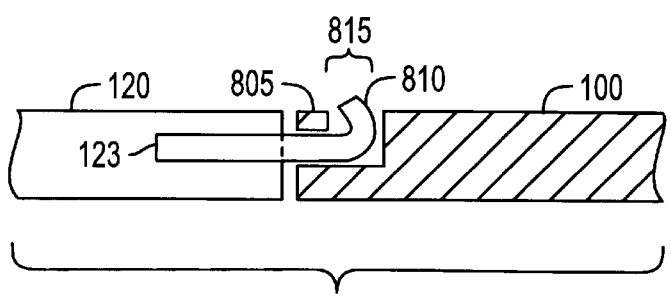

FIGS. 8A–8B show still another embodiment of an attachment device. This embodiment includes the embedded support ring 123. The support ring 123 includes an attachment portion in the form of a hinge hook 810 that extends from the perimeter of the mask seal 120. The mask shell 100 includes a corresponding attachment portion in the form of a hinge opening 815 and a hinge axle 805. The hinge hook 810 resides in the hinge opening 815, engages the hinge axle 805, and allows the mask seal 120 to rotate with respect to the mask shell 100. In addition, the hinge allows the mask seal 120 and the hinge hook 810 to be removed from the mask shell 100.

Figure 9A:
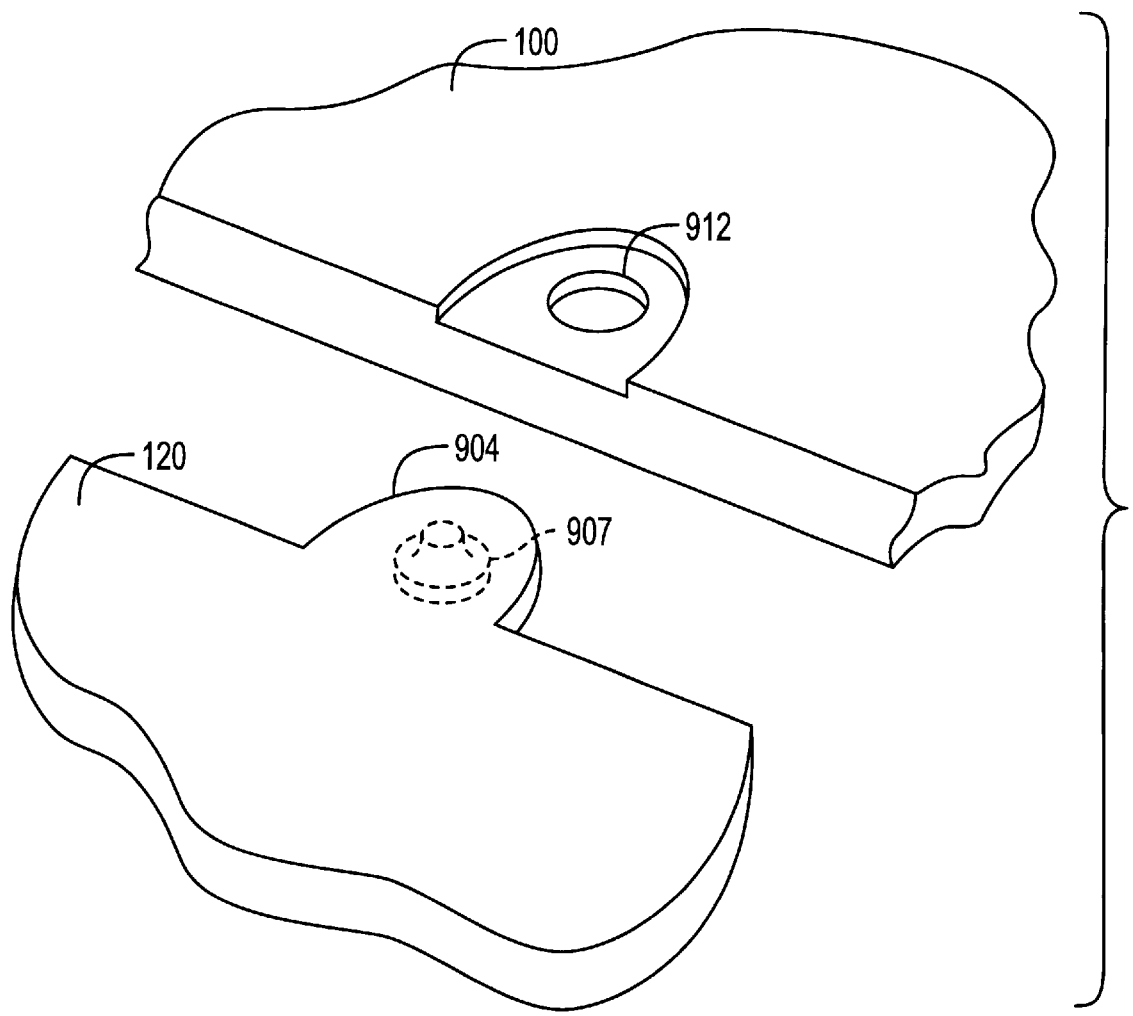
FIGS. 9A–9B show still another embodiment of an attachment device.
Figure 9B:
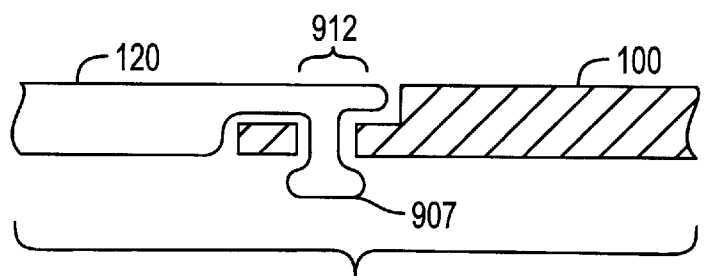

FIGS. 9A–9B show still another embodiment of an attachment device. In this embodiment the mask seal 120 includes an attachment portion in the form of an extended portion 904 of the mask seal 120 and a knob 907. The extended portion 904 extends beyond an intersection of the mask seal 120 and the mask shell 100. The knob 907 may be pressed through a corresponding attachment portion in the form of a hole 912 in the mask shell 100. The knob 907 engages the hole 912 to hold the mask seal 120 on the mask shell 100. The knob 907 is wider than the hole 912. The hole 912 may be recessed into the mask shell 100. In this embodiment, the knob 907 is oriented towards the inner portion of the mask shell 100, in contrast to FIG. 7, where the knob 707 is formed on the mask shell 100 and is oriented away from the inner portion of the mask shell 100.

Figure 10:
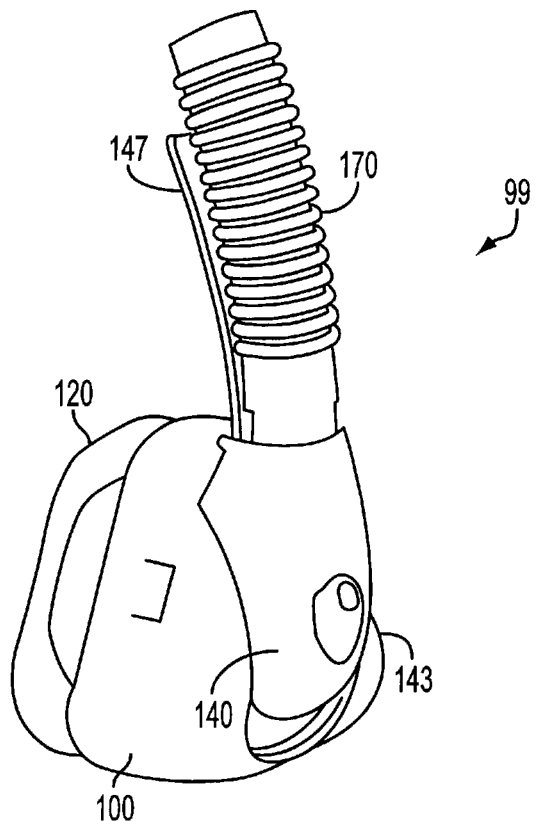
FIG. 10 shows a respirator mask of the present invention.

FIG. 10 shows a respirator mask 99 of the present invention. The respirator mask 99 includes a mask shell 100, a mask seal 120, and a movable interface 140. The mask shell 100 has a convex outer surface and may be formed of a rigid or semi-rigid material. The movable interface 140 includes a contoured opening adapted to fit against the mask shell 100 (see FIGS. 15 and 16), and further includes a vent port 143 and a headpiece slide 147. The movable interface 140 may be connected to a gas supply hose 170 that may provide the respirator mask with a gas or gas mixture which may include oxygen, anesthesia gas and/or one or more medications. The vent port 143 allows exhaled gas to be vented.

Figure 11:
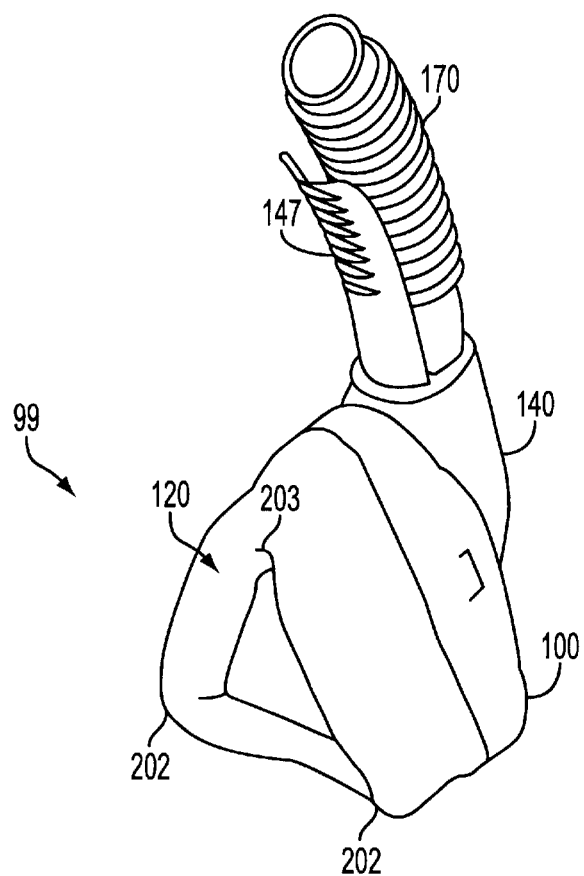
FIG. 11 shows another view of the respirator mask showing further detail of the mask seal.

FIG. 11 shows another view of the respirator mask 99 showing further detail of the mask seal 120. The mask seal 120 may be removably affixed to the mask shell 100. The mask seal 120 is elastomeric and is formed of a pliable, flexible material such as, for example, silicone. The mask seal 120 includes a flexible sidewall that extends from the mask shell 100 and mask seal regions. The mask seal 120 is easily deformed in order to form a seal against the face of the wearer. The flexibility of the mask seal 120 is dependent not only on the type of material but on the construction of the mask seal 120 that allows the mask seal to deform somewhat to fit the face of the wearer. This will be discussed in more detail below.

The mask seal 120 and the mask shell 100 are generally triangular in shape with a top corner 203 fitting over the bridge of the nose of the wearer and the two bottom corners 202 being located adjacent to the corners of the mouth of the wearer.

Figure 12:
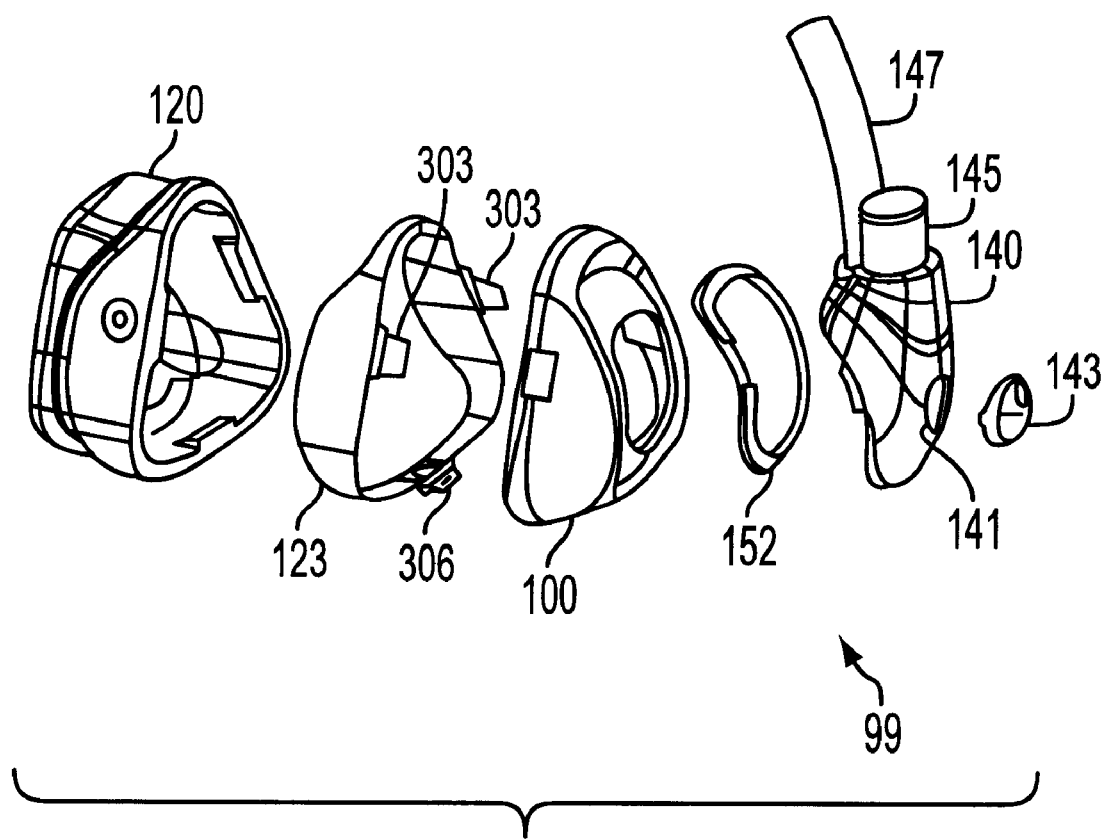
FIG. 12 shows an exploded view of the components of the respirator mask.

FIG. 12 shows an exploded view of the components of the respirator mask 99 including the mask seal 120, a support ring 123 that resides within the mask seal 120, the.mask shell 100, the movable interface 140, an interface gasket 152, a vent port aperture 141, the vent port 143, the headpiece slide 147, and a hose connector 145.

The support ring 123 is optional and resides within the mask seal 120. The support ring 123 may be molded into or inside the mask seal 120. The support ring 123 includes at least one attachment device 303, such as a tab or barbed tab, that allows the support ring 123 to be removably affixed to the mask shell 100, thereby joining the mask seal 120 to the mask shell 100. In addition, the support ring 123 may include a hinge hook 306 that may rotatably engage a hinge axle 805 (not shown) on the mask shell 100. Alternatively, the attachment device 303 may be any of the other previously described attachment devices. The at least one attachment device 303 is received by an attachment opening 405 located on the mask shell 100 (see FIG. 14).

The support ring 123 is semi-rigid or rigid, such as, for example, a support ring formed of a polycarbonate material. The support ring 123 is conformed to assist the mask seal 120 in retaining a predetermined shape. This includes keeping the mask seal 120 from ballooning outward under air pressure and maintaining a predetermined anatomically desired shape. The support ring 123 may provide added compressive force against the skin where it is needed, in addition to the compressive force provided by the mask seal 120, i.e., at the side of the nose, for example.

The support ring 123 also facilitates attachment of the mask seal 120 to the mask shell 100. The support ring 123 facilitates localized attachment by providing a rigid anchor or base for attachment devices, such as, for example, snaps or barbs.

Furthermore, the support ring 123 maintains the shape of the mask seal 120 while it is being handled, such as during removal, cleaning, and re-installation.

The interface gasket 152 fits between the movable interface 140 and the mask shell 100. The interface gasket 152 prevents gas leakage between the movable interface 140 and the mask shell 100 while facilitating the motion of the movable interface 140 on the mask shell 100.

The vent port 143 preferably snaps into the vent aperture 141 of the movable interface 140 and may be used to control the size of the vent aperture for CPAP venting (the vent port 143 may be provided in any suitable size).

The hose connector 145 is adapted to connect to the gas supply hose 170. The hose connector 145 may be of any suitable diameter.

The headpiece slide 147 allows the respirator mask to be attached to a headpiece (not shown) that holds the respirator mask in position on the head of the user. The headpiece may be a rigid or semi-rigid band that extends up and over the center of the user's head, ending in a region at a base of the skull. The gas supply hose 170 may travel up and over the head of the user, and may be fastened to the headpiece. The headpiece slide 147 preferably has a curved profile (see FIG. 16) that allows the respirator mask 99 to be positioned for a user's face but may be moved up or down without moving the respirator mask 99 closer to or farther away from the user's face as a result of the adjustment motion. In addition, the headpiece slide 147 may include a plurality of ratchet openings 148 (see FIG. 15) that serve as detent positions for positioning the respirator mask on the headpiece.

Figure 13:
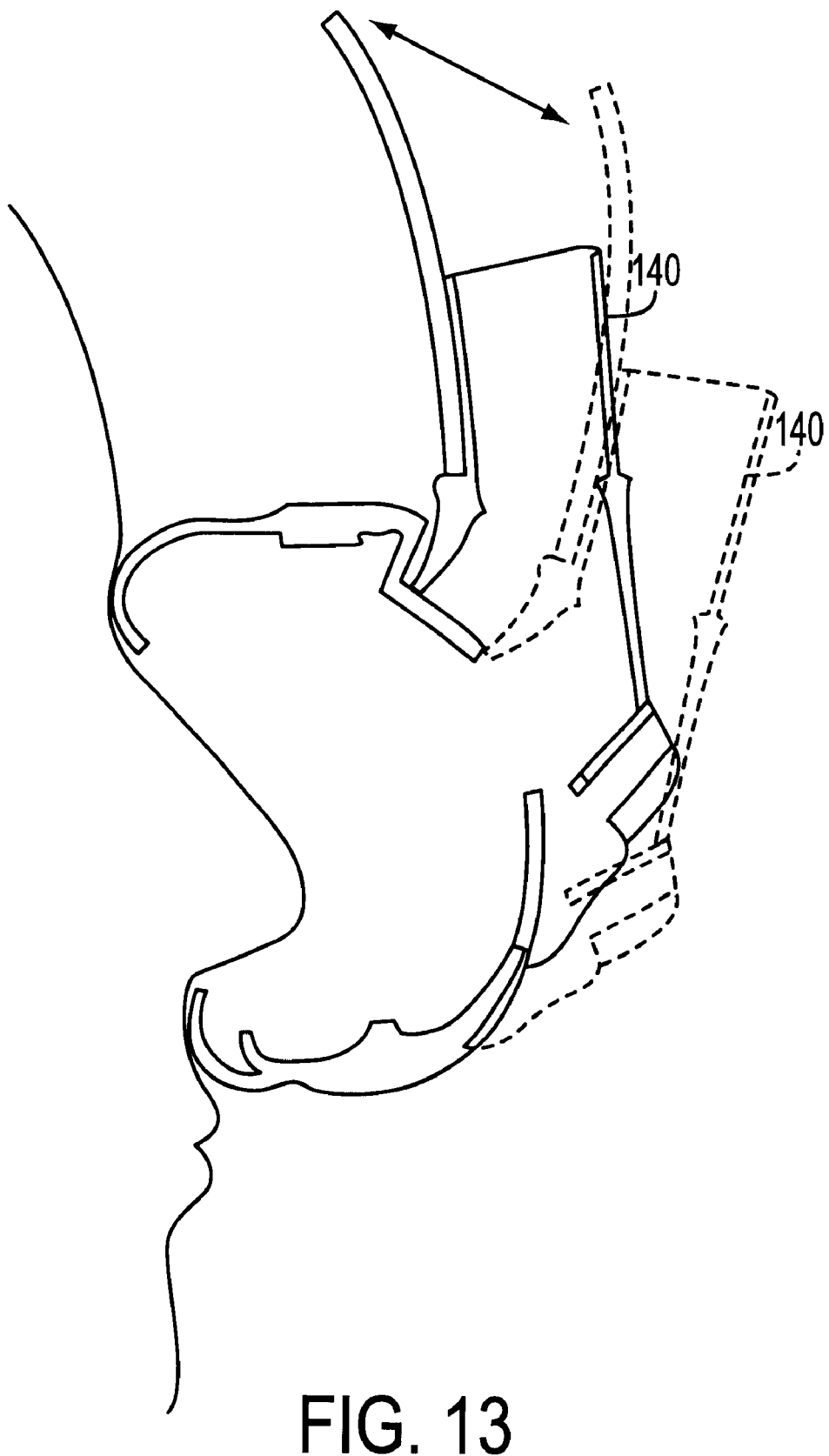
FIG. 13 shows a cross-sectional view of the respirator mask according to the invention illustrating the adjustment motion of the movable interface.

FIG. 13 shows a cross-sectional view of the respirator mask according to the invention illustrating the adjustment motion of the movable interface 140. The movable interface 140 pivots about a pivot center, implementing a goniometric pivot device. A goniometric pivot device is an angle measuring pivot or mechanism. The pivot center may be substantially within the interior volume of the mask shell 100 or the respirator mask 99. The movable interface 140 therefore allows an angular adjustment of the mask shell 100 with respect to a facial plane angle.

The movable interface 140 provides a benefit in that the movable interface 140 may be ergonomically activated by the user. In addition, the movable interface 140 has a low profile with respect to the face of the wearer, with the integral airway requiring little space. The movable interface 140 therefore combines a support function and an airway conduit into one mechanism. Furthermore, the movable interface 140 is minimally complex in order to provide ease of use and durability.

Figure 14:
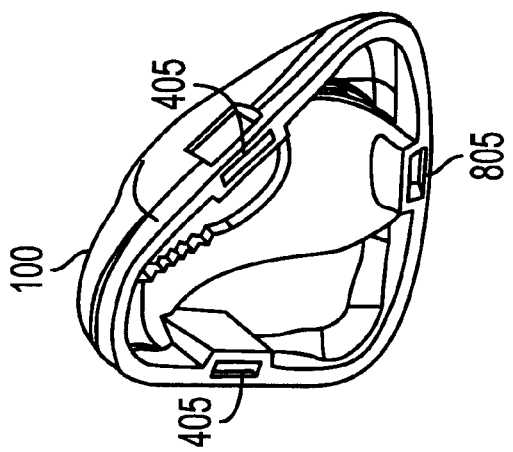
FIG. 14 is another view of the mask shell showing attachment openings used to attach the mask seal to the mask shell.

FIG. 14 is another view of the mask shell 100 showing the attachment openings 405 used to attach the mask seal 120 to the mask shell 100. In addition, at the bottom of the mask shell 100 may be located a hinge axle 805.

Figure 17:
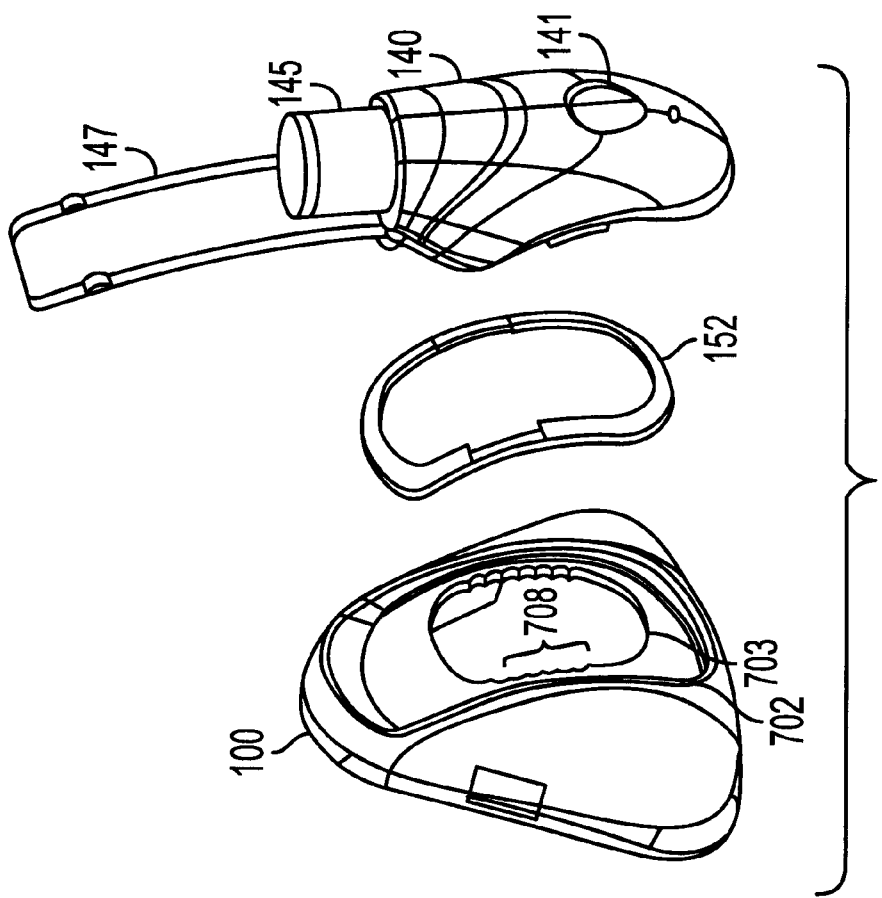
FIG. 17 shows the mask shell, the movable interface, and an interface gasket.
Figure 15:
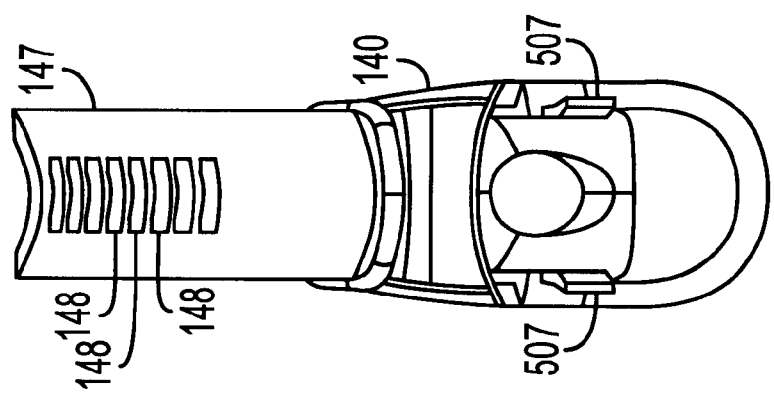
FIG. 15 shows a back view of the movable interface, showing two barbed tabs that are capable of engaging in the slot of the mask shell.

FIG. 15 shows a back view of the movable interface 140, showing two barbed tabs 507 that are capable of engaging in the slot 703 of the mask shell 100 (see FIG. 17). The barbed tabs 507 therefore function to hold the movable interface 140 onto the mask shell 100, while allowing the movable interface 140 to slide in the depression 702. Although two tabs 507 are shown, it should be understood that a different number of tabs or tabs of other sizes may be used.

Figure 16:
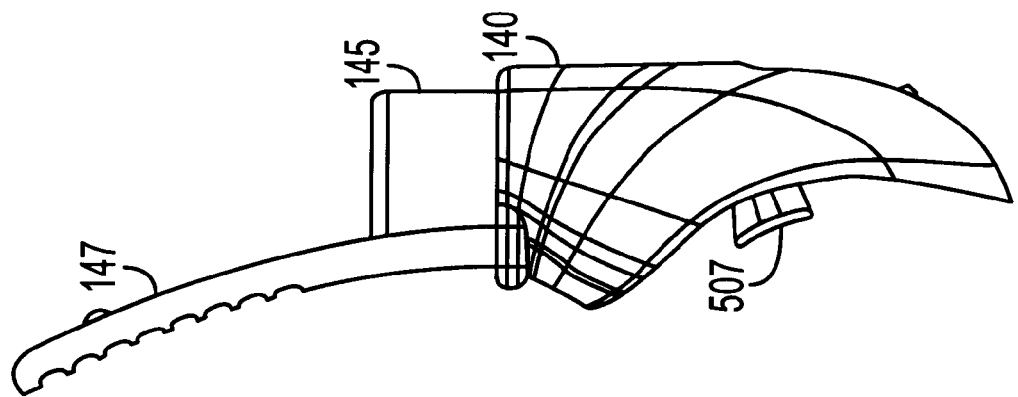
FIG. 16 shows a side view of the movable interface further illustrating the shape of the barbed tabs.

FIG. 16 shows a side view of the movable interface 140 further illustrating the shape of the barbed tabs 507.

FIG. 17 shows the mask shell 100, the movable interface 140, and the interface gasket 152. As can be seen from the figure, the mask shell 100 includes a depression 702 in which the movable interface 140 may vertically pivot or slide. The mask shell 100 also includes a slot 703 over which the movable interface 140 fits. In addition, the slot 703 includes a plurality of detents 708, which interact with the tabs 507 extending from the mask shell 140. The detents 708 enable the movable interface 140 to be set at predetermined positions.

As can be seen from this figure, the outer surface of the mask shell 100 is substantially rounded or convex, as is the contact surface of the movable interface 140 (i.e., the movable interface 140 includes a contoured opening). The movable interface 140, therefore, fits against the mask shell 100 and slides over the slot 703.

Figure 18:
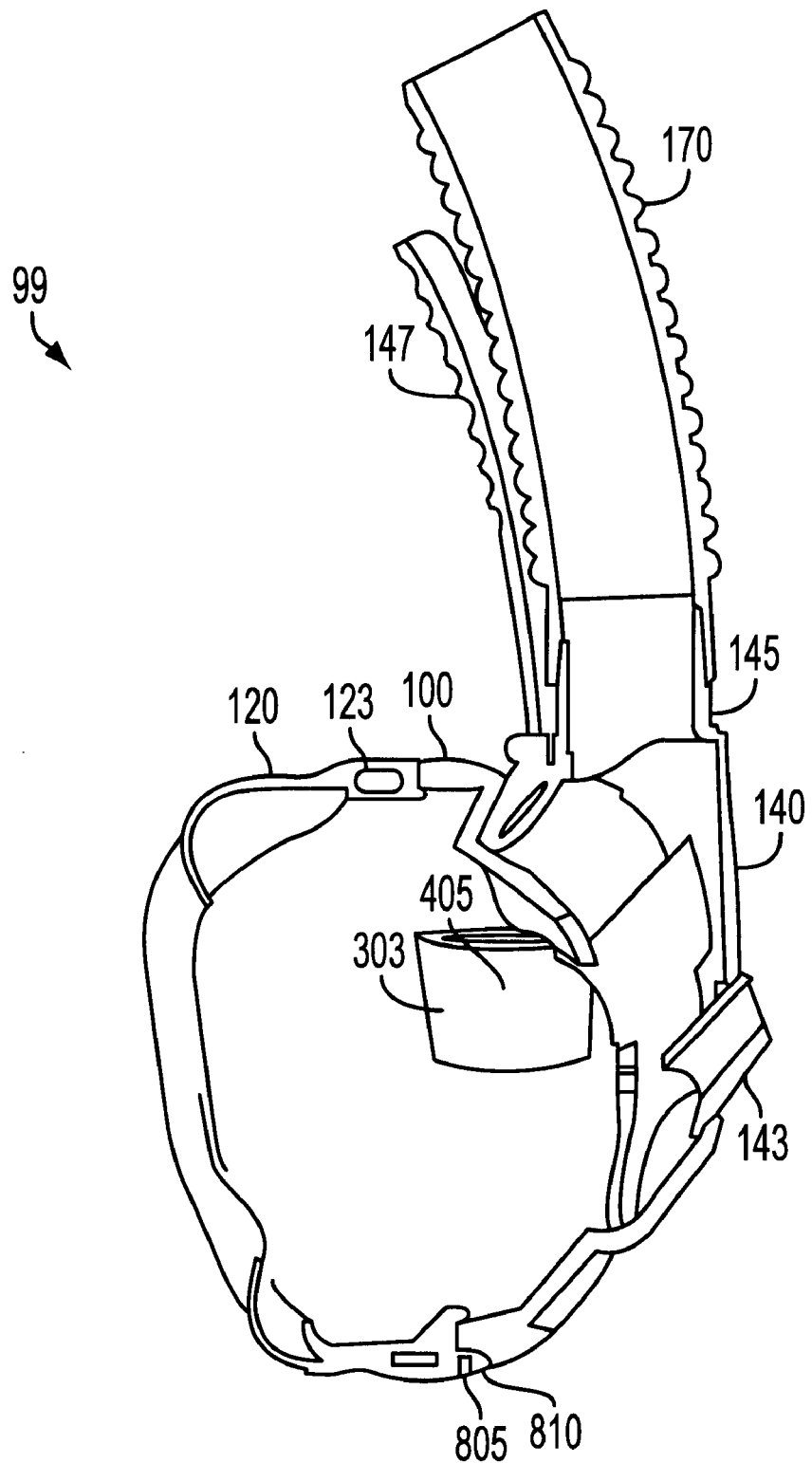
FIG. 18 shows a cross-section of the respirator mask illustrating how the mask seal mates to the mask shell.

FIG. 18 shows a cross-section of the respirator mask 99 illustrating how the mask seal 120 mates to the mask shell 100. The figure further illustrates how the movable interface 140 fits onto the mask shell 100. As can be seen from the figure, several openings 405 exist on the mask shell 100 into which the attachment devices 303 fit, in order to removably affix the mask seal 120 to the mask shell 100. In the preferred embodiment there are two sets of attachment devices 303 and openings 405, and additionally the hook 306 on the mask seal 120 and the corresponding axle 805 on the mask shell 100 (see also FIGS. 12 and 14).

To mate the mask seal 120 of the preferred embodiment to the mask shell 100, the mask seal 120 is angled relative to the mask shell 100 and the hinge hook 810 is placed over the hinge axle 805. The mask seal 120 is then rotated up into contact with the mask shell 100, with the attachment devices 303 fitting or snapping into the corresponding openings 405.

It should be understood that the devices referred to as the attachment devices 303 and the openings 405 may be any of the attachment devices shown and discussed in FIGS. 4–9.

Figure 19:
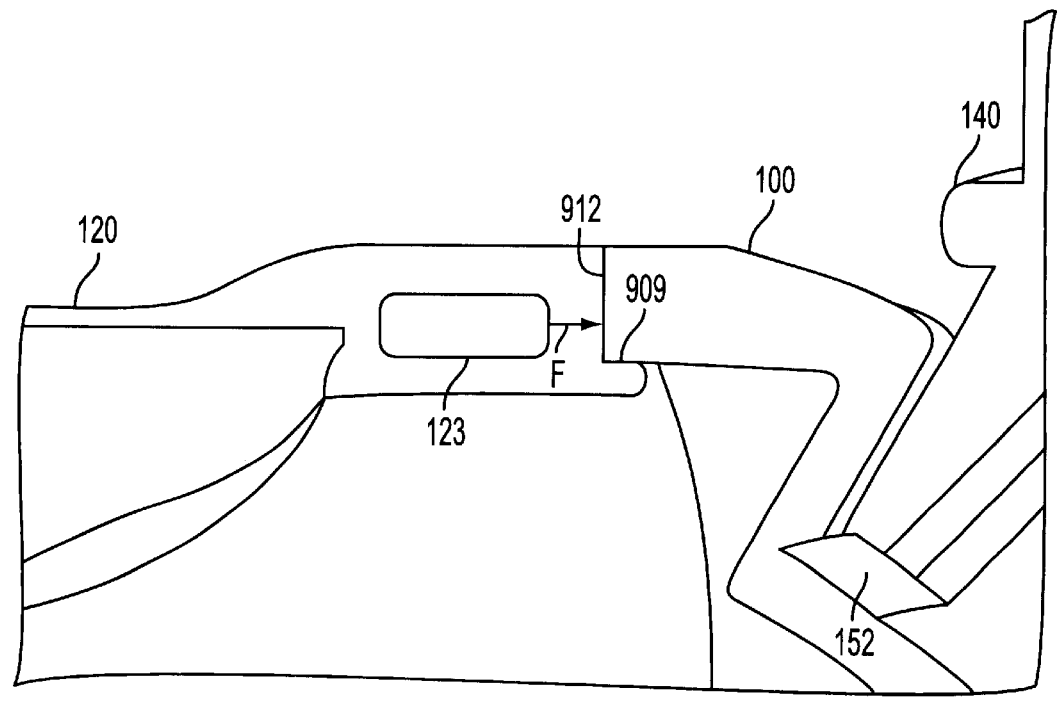
FIG. 19 shows detail of a junction of the mask seal and the mask shell, further showing a flange.

FIG. 19 shows detail of a junction of the mask seal 120 and the mask shell 100, further showing a flange 909. The flange 909 is formed on an inner perimeter of a mating surface 912 of the mask seal, with the mating surface 912 being a surface that contacts the mask shell when the respirator mask is assembled. The support ring 123 asserts an inward compressive force F against the surface 912. The flange 909 assists the formation of an essentially gas or air tight seal around an inner circumference of the mask shell 100.

Figure 20:
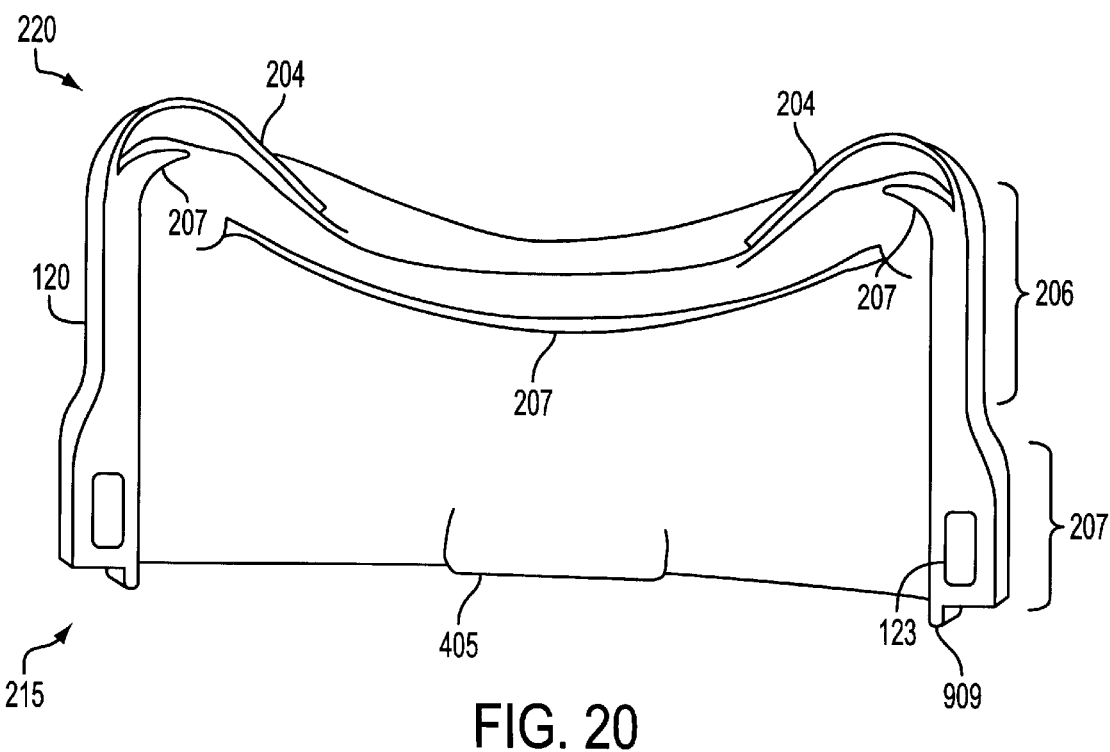
FIG. 20 shows a cross section of the mask seal and the support ring.

FIG. 20 shows a cross section of the mask seal 120 and the support ring 123. The figure shows how the side wall of the mask shell 120 thins out above the support ring 123, having a thicker region 207 and a thinner region 206. The side wall has a proximal end 215 and a distal end 220, with the proximal end 215 being adjacent to the support ring 123. At the distal end 220 is formed an outer seal portion 204 which is rounded and preferably curves inwardly toward the center of the mask seal 120. The material of the outer seal portion 204 is relatively thin. The mask seal 120 also includes an inner seal portion 207 that is also somewhat rounded over and is thicker than the outer seal portion 204.

The outer seal portion 204 is continuous around the opening of the mask seal 120. In contrast, the inner seal portion 207 is non-continuous at the corners 202 and 203 (see FIG. 11). This allows the outer seal portion 204 to deform more in the areas of the bridge of the nose and the corners of the mouth, where more deformation is likely to be needed.

The inner seal portion 207, being less rounded over and thicker than the outer seal portion 204, deforms less easily. The inner seal portion 207 performs a valuable function in that when the outer seal portion 204 contacts the inner seal portion 207, the inner seal portion 207 provides a greater compressive force against the face of the wearer. The inner seal portion 207 therefore provides more stiffness and helps to round over the outer seal portion 204.

Figure 21:
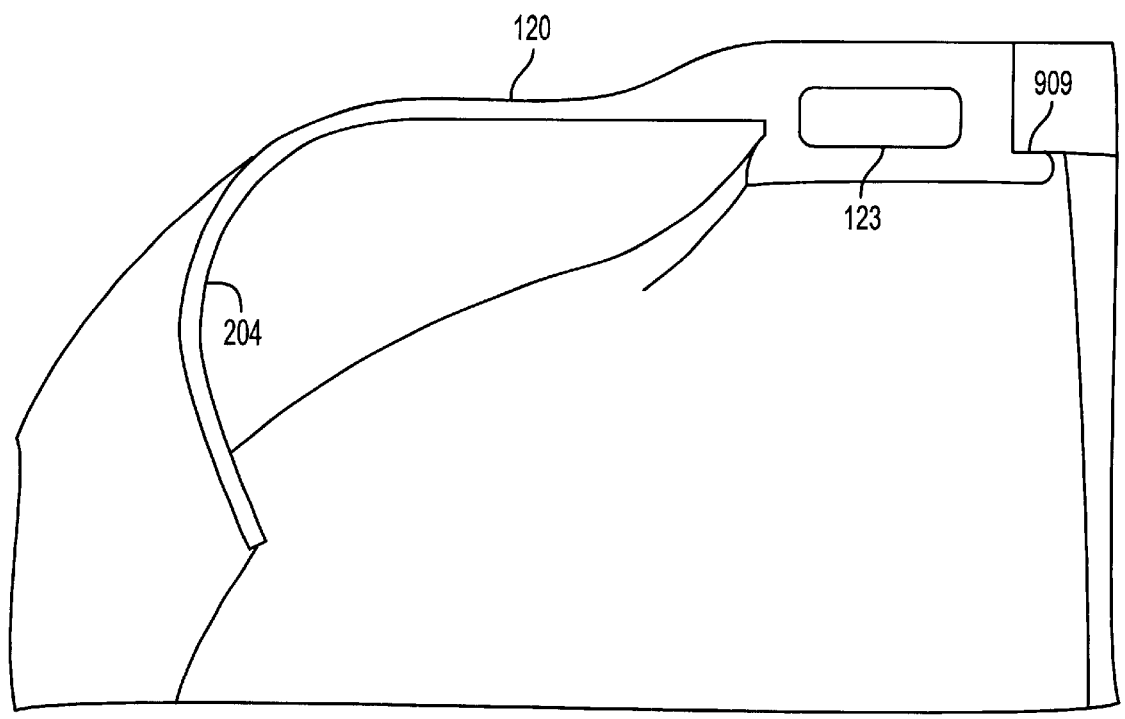
FIG. 21 is an enlarged cross-section of the mask seal in the region of one of the corners, where the inner seal does not exist.

FIG. 21 is an enlarged cross-section of the mask seal 120 in the region of one of the corners 202 or 203, where the inner seal does not exist.

Figure 22:
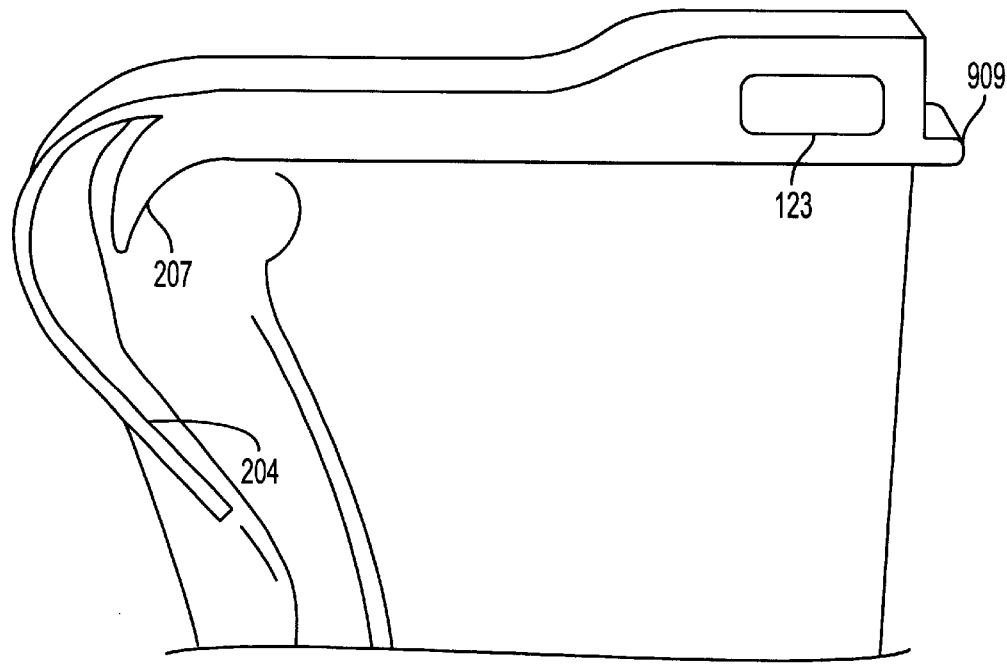
FIG. 22 is an enlarged cross-section of the mask seal that includes the inner seal region.

FIG. 22, in contrast, is an enlarged cross-section of the mask seal 120 that includes the inner seal portion 207, such as a portion of the mask seal 120 away from the corners 202 or 203.

While the invention has been described in detail above, the invention is not intended to be limited to the specific embodiments as described. It is evident that those skilled in the art may now make numerous uses and modifications of and departures from the specific embodiments described herein without departing from the inventive concepts.

What is claimed is:

1. A respirator mask seal and shell, comprising:
    a mask shell having a face opening, a slot for air passage, and at least one attachment portion spaced around said face opening;
    a movable interface having a hose connector and a contoured opening adapted to fit against said mask shell, said contoured opening of said movable interface being slidable over said slot and capable of being positioned on said mask shell over a predetermined range;
    a mask seal comprising a flexible sidewall having distal and proximal ends and including a rounded outer seal portion located on said distal end of said sidewall, a rounded inner seal portion located between said distal and proximal ends, said inner seal portion being thicker than said outer seal portion and being non-continuous around an inner surface of said mask seal, and a support ring embedded in said sidewall adjacent said proximal end, said support ring including at least one attachment portion adapted to engage said at least one attachment portion of said mask shell, with said proximal end of said mask seal being capable of being removably affixed to said mask shell;
    wherein said movable interface is capable of being positionally adjusted on said mask shell so to be adaptable to a wearer, and wherein in use said mask seal is capable of being inwardly deformed by contact with a face region of said wearer.

2. The respirator mask seal and shell of claim 1, wherein said mask shell further includes a depression, with said movable interface capable of vertically sliding within said depression.

3. The respirator mask seal and shell of claim 1, wherein said movable interface further includes a headpiece slide formed as part of and extending from a portion of said movable interface.

4. The respirator mask seal and shell of claim 1, wherein said movable interface further includes a vent aperture.

5. The respirator mask seal and shell of claim 1, wherein said movable interface further includes a vent aperture, said vent aperture being capable of retaining a vent port having a predetermined vent hole size.

6. The respirator mask seal and shell of claim 1, further including an interface gasket between said movable interface and said mask shell.

7. The respirator mask seal and shell of claim 1, said movable interface further comprising a plurality of barbed tabs located on said contoured opening of said movable interface, wherein said plurality of barbed tabs are adapted to snap into said slot in said mask shell and slide in said slot to allow said movable interface to move on said mask shell.

8. The respirator mask seal and shell of claim 1, wherein said hose connector is substantially vertically oriented with respect to said mask.

9. The respirator mask seal and shell of claim 1, wherein said proximal end of said mask seal includes a flange that is formed on an inner perimeter of a mating surface of said mask seal, wherein said flange fits inside said mask shell to form a gas seal.

10. The respirator mask seal and shell of claim 1, wherein said mask seal comprises an elastomeric material.

11. The respirator mask seal and shell of claim 1, wherein said mask seal comprises silicone.

12. The respirator mask seal and shell of claim 1, wherein said rounded outer seal curves inwardly toward an interior portion of said mask.

13. The respirator mask seal and shell of claim 1, wherein said rounded inner seal curves inwardly toward an interior portion of said mask.

14. The respirator mask seal and shell of claim 1, wherein said inner seal portion is adapted for compressing said outer seal portion against a face of a wearer.

15. The respirator mask seal and shell of claim 1, wherein said support ring comprises a semi-rigid material.

16. The respirator mask seal and shell of claim 1, wherein said support ring comprises a rigid material.

17. The respirator mask seal and shell of claim 1, wherein said support ring is molded inside said side wall of said mask seal.

18. The respirator mask seal and shell of claim 1, wherein said support ring includes at least one elongate extension member that extends beyond a portion of said mask seal and engages a corresponding cavity on said mask shell.

19. The respirator mask seal and shell of claim 1, wherein said support ring of said mask seal further comprises a hinge hook and said mask shell further comprises a hinge axle, and wherein said hinge hook rotatably engages said hinge axle when said mask seal is brought into position against said mask shell.

20. The respirator mask seal and shell of claim 1, wherein said at least one attachment portion of said mask seal comprises a barbed tab.

21. A respirator mask, comprising:
    a mask shell having a convex outer surface and a slot therein; and
    a movable interface that movably pivots on said convex outer surface, said movable interface including a hose connector adapted to receive a gas supply hose and further including an interior passage that communicates a gas from said hose connector to said slot and to an interior region of said mask shell;
    wherein said movable interface allows an angular adjustment of said mask shell with respect to a facial plane angle of a user.

22. The respirator mask of claim 21, further including an interface gasket positioned between said movable interface and said mask shell, said interface gasket facilitating motion of said movable interface on said mask shell and preventing a gas leakage between said movable interface and said mask shell.

23. The respirator mask of claim 21, wherein said movable interface has a pivot center substantially within a volume of said mask shell.

24. The respirator mask of claim 21, said movable interface further including a plurality of barbed tabs that engage an edge of said slot in said mask shell and movably hold said movable interface against said mask shell.

* * * * *